US008470888B2

(12) United States Patent
Henrich et al.

(10) Patent No.: US 8,470,888 B2
(45) Date of Patent: Jun. 25, 2013

(54) BOTRYLLAMIDES AND METHOD OF INHIBITING PGP IN A MAMMAL AFFLICTED WITH CANCER

(75) Inventors: Curtis J. Henrich, Rockville, MD (US); Heidi R. Bokesch, Frederick, MD (US); Laura K. Cartner, Middletown, MD (US); Richard W. Fuller, Fairfield, PA (US); Kirk R. Gustafson, Frederick, MD (US); Kentaro Takada, Yokohama (JP); James B. McMahon, Frederick, MD (US); Susan E. Bates, Bethesda, MD (US); Robert W. Robey, Laurel, MD (US); Suneet Shukla, Rockville, MD (US); Suresh V. Ambudkar, Gaithersburg, MD (US); Michael C. Dean, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 259 days.

(21) Appl. No.: 12/811,144

(22) PCT Filed: Dec. 29, 2008

(86) PCT No.: PCT/US2008/088446
§ 371 (c)(1),
(2), (4) Date: Aug. 2, 2010

(87) PCT Pub. No.: WO2009/088831
PCT Pub. Date: Jul. 16, 2009

(65) Prior Publication Data
US 2010/0317732 A1   Dec. 16, 2010

Related U.S. Application Data

(60) Provisional application No. 61/018,758, filed on Jan. 3, 2008.

(51) Int. Cl.
*A61K 31/12* (2006.01)
*C07C 59/86* (2006.01)

(52) U.S. Cl.
USPC .......................................... 514/679; 562/459

(58) Field of Classification Search
None
See application file for complete search history.

(56) References Cited

U.S. PATENT DOCUMENTS

| 4,235,871 | A | 11/1980 | Papahadjopoulos et al. |
| 4,501,728 | A | 2/1985 | Geho et al. |
| 4,837,028 | A | 6/1989 | Allen |
| 5,019,369 | A | 5/1991 | Presant et al. |

FOREIGN PATENT DOCUMENTS

| EP | 1 864 972 A1 | 12/2007 |
| WO | 02/053138 A2 | 7/2002 |
| WO | 2006/031614 A2 | 3/2006 |
| WO | 2008/039254 A2 | 4/2008 |
| WO | 2008/062466 A2 | 5/2008 |
| WO | 2009/088831 A2 | 7/2009 |

OTHER PUBLICATIONS

McDonald et al., Tetrahedron, vol. 51, No. 18, pp. 5237-5244.*
Rao et al., J. Nat. Prod., 2004, 67-1064-1066.*
McKay et al., Journal of Natural Products (2005), 68(12), 1776-1778.*
Ahmed-Belkacem et al., *Anti-Cancer Drugs*, 17 (3), 239-243 (2006).
Ahmed-Belkacem et al., *Cancer Res.*, 65 (11), 4852-4860 (2005).
Allen et al., *Mol. Cancer Ther.*, 1 (6), 417-425 (2002).
Alvarez et al., *Mol. Pharmacol.*, 54, 802-814 (1998).
Benderra et al., *Clin. Cancer Res.*, 11 (21), 7764-7772 (2005).
Boumendjel et al., *Med. Res. Rev.*, 25 (4), 453-472 (2005).
Breedveld et al., *Cancer Res.*, 65 (7), 2577-2582 (2005).
Damiani et al., *Haematologica*, 91 (6), 825-828 (2006).
Dean et al., *Nat. Rev. Cancer.*, 5, 275-284 (2005).
Diestra et al., *J. Pathol.*, 198, 213-219 (2002).
Henrich et al., *J. Biomol. Screen.*, 11 (2), 176-183 (2006).
Henrich et al., *Mol. Cancer Ther.*, 6 (12), 3271-3278 (2007).
Holbeck, *Eur. J. Cancer*, 40, 785-793 (2004).
Horenstein et al., *J. Am. Chem. Soc.*, 111 (6), 6242-6246 (1989).
Ikeda et al., *Int. J. Cancer*, 45, 508-513 (1990).
Ikeda, *Med. J. Kagoshima Univ.*, 42 (4), 367-377 (1991), (English Abstract).
Jonker et al., *J. Natl. Cancer Inst.*, 92 (20), 1651-1656 (2000).
Jonker et al., *Proc. Natl. Acad. Sci. USA*, 99 (24), 15649-15654 (2002).
Kim et al., *Tetrahedron Letters*, 31 (49), 7119-7122 (1990).
Krishnamurthy et al., *Annu. Rev. Pharmacol. Toxicol.*, 46, 381-410 (2006).
Kruijtzer et al., *J. Clin. Oncol.*, 20 (13), 2943-2950 (2002).
Marchand et al., *Tetrahedron*, 25 (5), 937-954 (1969), (English Abstract).
McDonald et al., *Tetrahedron*, 51 (18), 5237-5244 (1995).
Oltz et al., *J. Am. Chem. Soc.*, 110 (18), 6162-6172 (1988).
Özvegy-Laczka et al., *J. Biol. Chem.*, 280 (6), 4219-4227 (2005).
Phuwapraisirisan et al., *Bioorg. Med. Chem. Let.*, 18 (18), 4956-4958 (2008).

(Continued)

*Primary Examiner* — Sreeni Padmanabhan
*Assistant Examiner* — Svetlana M. Ivanova
(74) *Attorney, Agent, or Firm* — Leydig, Voit & Mayer, Ltd.

(57) ABSTRACT

Disclosed are methods of enhancing the chemotherapeutic treatment of tumor cells, reducing resistance of a cancer cell to a chemotherapeutic agent, a method of inhibiting ABCG2, Pgp, or MRP1 in a mammal afflicted with cancer, and a method of increasing the bioavailability of an ABCG2 substrate drug in a mammal. The methods comprise administering effective amounts of certain compounds to the mammal, for example, a compound of the formula (I): Formula (I), wherein $R^1$, $R^2$, $R^3$, $X^1$, $X^2$, $X^3$, a, and b are as described herein. Uses of these compounds in the preparation of a medicament are also disclosed. Also disclosed are compounds of formula (II), pharmaceutical compositions comprising such compounds and uses thereof.

(I)

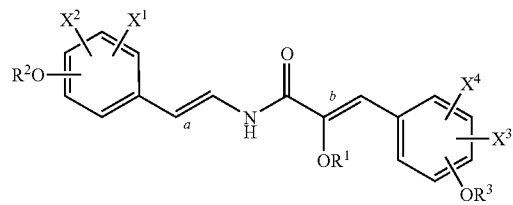

3 Claims, 2 Drawing Sheets

OTHER PUBLICATIONS

Plasschaert et al., *Leukemia and Lymphoma*, 45 (4), 649-654 (2004).
Price et al., *Antimicrobial Agents and Chemotherapy*, 161, 95-99 (1963).
Rabindran et al., *Cancer Res.*, 58, 5850-5858 (1998).
Rao et al., *J. Nat. Prod.*, 67 (6), 1064-1066 (2004).
Robey et al., *Biochim. Biophys. Acta*, 1512, 171-182 (2001).
Robey et al., *Br. J. Cancer*, 89, 1971-1978 (2003).
Robey et al., *Cancer Metastasis Rev.*, 26, 39-57 (2007).
Robey et al., *Cancer Res.*, 64, 1242-1246 (2004).
Robey et al., *Clin. Cancer Res.*, 7, 145-152 (2001).
Sakurai et al., *J. Antibio.*, 55 (8), 685-692 (2002).
Sarkadi et al., *Physical. Rev.*, 86, 1179-1236 (2006).
Scudiero et al., *Cancer Res.*, 48, 4827-4833 (1988).
Shoemaker, *Nat. Rev. Cancer*, 6 (10), 813-823 (2006).
Shukla et al., *Biochemistry*, 45 (29), 8940-8951 (2006).
Skehan et al., *J. Natl. Cancer Inst.*, 82 (13), 1107-1112 (1990).
Stewart et al., *Cancer Res.*, 64, 7491-7499 (2004).
Stonard et al., *Canada J. Chem.*, 58 (20), 2121-2126 (1980).
Szakács et al., *Nat. Rev. Drug Dis.*, 5 (3), 219-234 (2006).
Szoka et al., *Ann. Rev. Biophys. Bioeng.*, 9, 467-508 (1980).
Takano et al., *Pharmacol. Ther.*, 109, 137-161 (2006).
Uggla et al., *Leuk Res.*, 29 (2), 141-146 (2005).
Wasserman et al., *Cancer*, 36, 1258-1268 (1975).
Wilson et al., *Blood*, 108, 685-696 (2006).
Xu et al., *Curr. Med. Chem.*, 14, 689-701 (2007).
Yoh et al., *Clin. Cancer Res.*, 10, 1691-1697 (2004).
Zhang et al., *J. Antibiot*, 60 (3), 204-210 (2007).
Zhang et al., *Mol. Pharmacol.*, 65 (5), 1208-1216 (2004).

\* cited by examiner

BOTRYLLAMIDES AND METHOD OF INHIBITING PGP IN A MAMMAL AFFLICTED WITH CANCER

CROSS-REFERENCE TO A RELATED APPLICATION

This application claims the benefit of U.S. Provisional Patent Application No. 61/018,758, filed Jan. 3, 2008, the disclosure of which is incorporated by reference.

BACKGROUND OF THE INVENTION

Multidrug resistance has long been recognized as a major obstacle to successful cancer chemotherapy. The multidrug resistance transporter ABCG2 (or Breast Cancer Resistance Protein 1, BCRP1), a member of the ABC (ATP-binding cassette) family of membrane transport proteins, is believed to form a part of the maternal-fetal barrier, the blood-brain barrier, and is known to limit oral absorption of some drugs (Robey et al., *Cancer Metastasis Rev.*, 26: 39-57 (2007)). The normal physiologic functions of ABCG2 may be related to transport of a variety of natural substances to prevent intracellular accumulation of toxic compounds. ABCG2 is also an important mediator of resistance to a variety of anti-cancer drugs, including mitoxantrone, topotecan, irinotecan, flavopiridol, and methotrexate (Sarkadi et al., *Physiol. Rev.*, 86: 1179-1236 (2006); Krishnamurthy et al., *Annu. Rev. Pharmacol. Toxicol.*, 46: 381-410 (2006); Szakacs et al., *Nat. Rev. Drug Discov.*, 5: 219-34 (2006); and Xu et al., *Curr. Med. Chem.*, 14: 689-701 (2007)). Thus, inhibitors of ABCG2 activity could have important oncologic and pharmacologic applications.

Unfortunately, few, if any, clinically useful inhibitors of ABCG2 activity have been reported. Thus, there exists a desire for compounds that can inhibit ABCG2 and in turn, increase the efficacy of adjuvant chemotherapy.

BRIEF SUMMARY OF THE INVENTION

The invention provides a method of enhancing the chemotherapeutic treatment of tumor cells in a mammal with a chemotherapeutic agent, which method comprises administering to the mammal an effective amount of the chemotherapeutic agent in conjunction with an effective amount of a compound described herein that inhibits ABCG2 protein.

In an embodiment, the invention provides a method of reducing resistance of a cancer cell to a chemotherapeutic agent by inhibiting ABCG2 in a mammal, which method comprises administering to the mammal an effective amount of a compound described herein.

The invention further provides a method of inhibiting ABCG2, Pgp, and/or MRP1 in a mammal afflicted with cancer, which method comprises administering to the mammal an effective amount of a compound described herein.

The invention also provides a method of increasing the bioavailability of an ABCG2 substrate drug in a mammal, which method comprises administering to the mammal an effective amount of the ABCG2 substrate drug in conjunction with an effective amount of a compound described herein that inhibits ABCG2 protein.

The invention also provides uses of compounds described herein in the preparation of a medicament for (i) enhancing the chemotherapeutic treatment of tumor cells in a mammal in combination with a chemotherapeutic agent, (ii) inhibiting ABCG2 protein in a cancer patient, (iii) reducing drug resistance of a chemotherapeutic agent in a cancer patient, (iv) increasing the bioavailability of an ABCG2 substrate drug in a cancer patient, (v) inhibiting MRP1 in a cancer patient, or (vi) inhibiting Pgp in a cancer patient.

The invention also provides novel compounds of formula (II), described below, pharmaceutical compositions comprising such compounds, and their various uses.

DETAILED DESCRIPTION OF THE INVENTION

Figure 1:
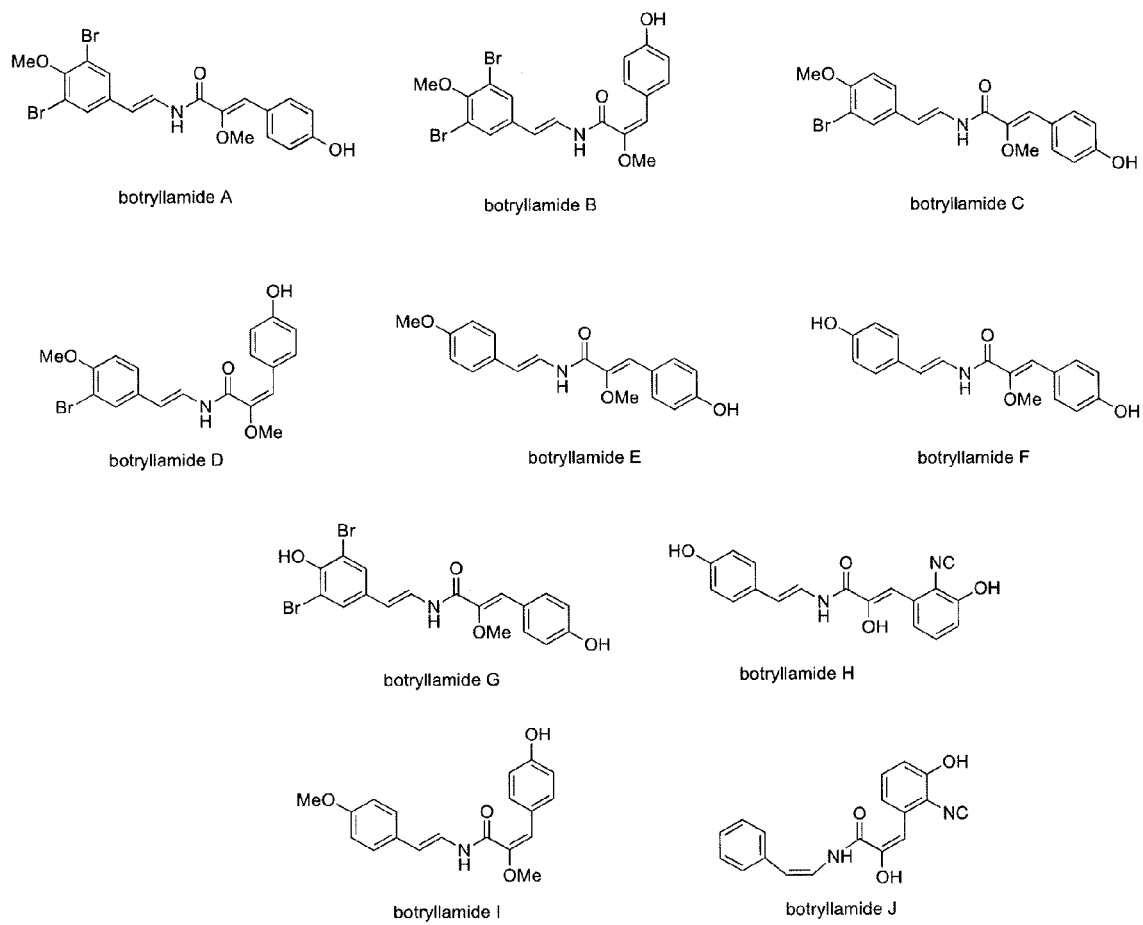
FIG. 1 depicts the formulas of certain botryllamides in accordance with an embodiment of the invention.
Figure 2:
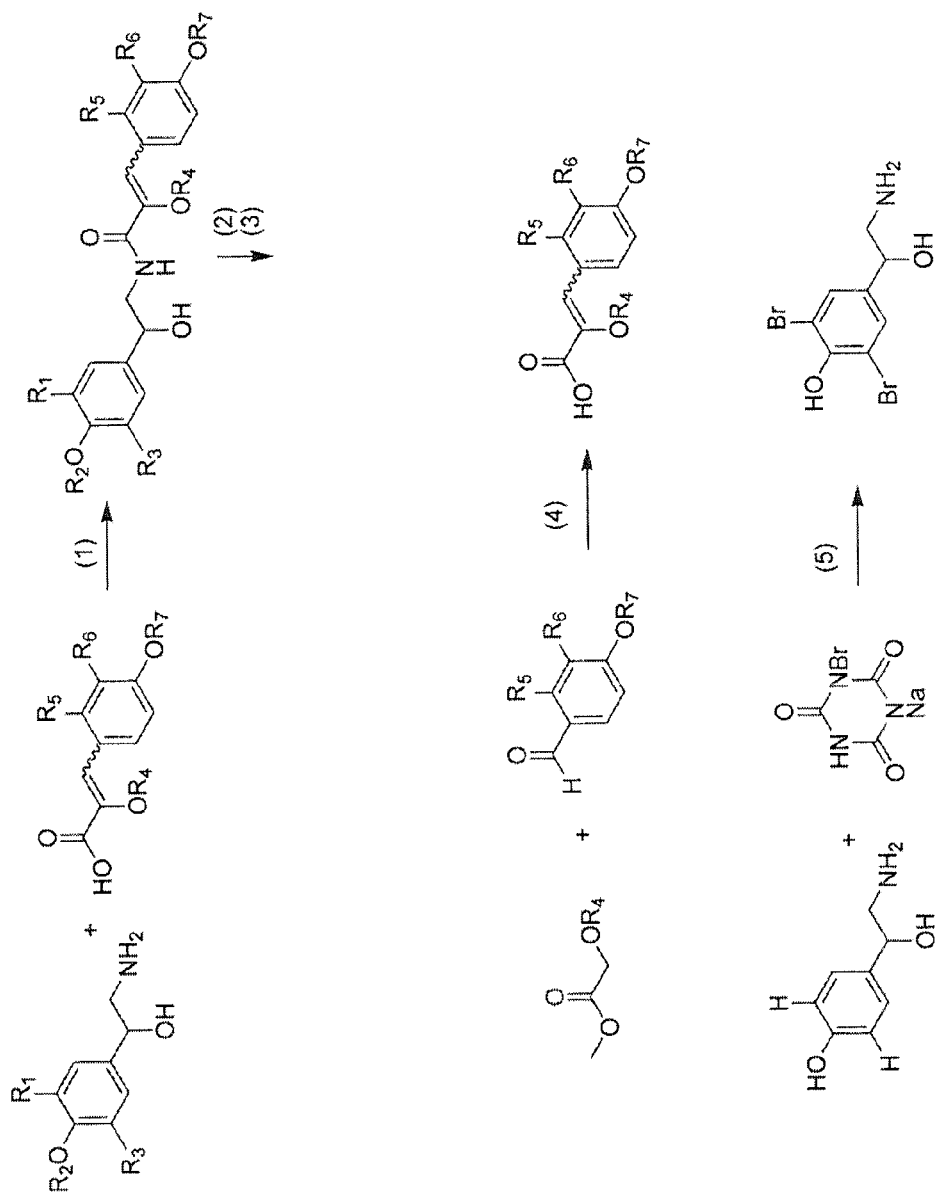
FIG. 2 depicts a reaction scheme to prepare compounds of formula (II) in accordance with an embodiment of the invention: (1) is a condensation reaction; (2) acetylation with acetic anhydride and pyridine; (3) dehydration: DMSO, $K_2CO_3$, 98° C.; (4) NaOMe, MeOH, reflux or t-BuOK, THF, −40° C.; (5) octopamine HCl plus BICA-Na in 60% $H_2SO_4$.

The invention provides, in accordance with an embodiment, a method of enhancing the chemotherapeutic treatment of tumor cells in a mammal with a chemotherapeutic agent, which method comprises administering to the mammal an effective amount of the chemotherapeutic agent in conjunction with an effective amount of a compound to inhibit ABCG2 protein, said compound being a compound of formula (I), to inhibit ABCG2 protein:

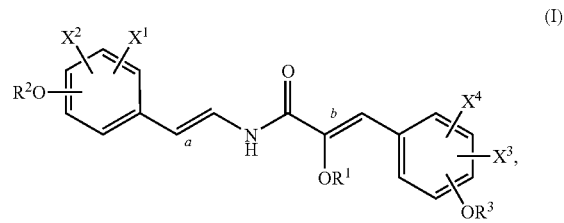

wherein $R^1$, $R^2$, and $R^3$ are independently selected from the group consisting of hydrogen, $C_1$-$C_6$ alkyl, $C_3$-$C_8$ cycloalkyl, hydroxy $C_1$-$C_6$ alkyl, halo $C_1$-$C_6$ alkyl, and $C_1$-$C_6$ alkyl carbonyl;

$X^1$ and $X^2$ are independently selected from the group consisting of hydrogen, halo, $C_1$-$C_6$ alkyl, $C_1$-$C_6$ alkoxy, $C_3$-$C_8$ cycloalkyl, hydroxy $C_1$-$C_6$ alkyl, halo $C_1$-$C_6$ alkyl, $C_1$-$C_6$ alkyl carbonyl, $C_2$-$C_6$ alkenyl, $C_2$-$C_6$ alkynyl, $C_6$-$C_{11}$ aryl, $C_3$-$C_7$ heteroaryl, $C_6$-$C_{12}$ aryloxy, CNS, $C_1$-$C_6$ alkoxy carbonyl, $C_1$-$C_6$ alkylthio, mercapto (SH), amido, formyl, and nitro; and $X^3$ and $X^4$ are independently any of $X^1$ and $X^2$, cyano, or isonitrile; and double bond "a" can be cis or trans and double bond "b" can be Z or E;

with the proviso that the compound is not botryllamide C, whereupon the chemotherapeutic treatment is enhanced.

By "enhancing the chemotherapeutic treatment" is meant that the chemotherapeutic agent has a greater effect (e.g., at least a 5% increase, at least a 10% increase, at least a 20% increase, at least a 30% increase, at least a 40% increase, at least a 50% increase, at least a 60% increase, at least a 70% increase, at least an 80% increase, etc.) in the presence of at least one compound described herein than in the absence of that compound. Since ABCG2 is a mediator of resistance, if a compound described herein inhibits ABCG2, the cancerous cell is less resistant to the chemotherapeutic agent, thereby making it more susceptible to the cytotoxicity of the agent.

The present invention also provides a method of reducing resistance of a cancer cell to a chemotherapeutic agent by inhibiting ABCG2 in a mammal, which method comprises administering to the mammal an effective amount of a compound of formula (I) to inhibit ABCG2 protein:

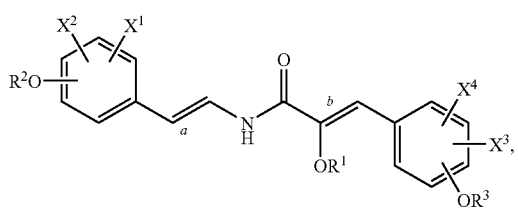
(I)

wherein $R^1$, $R^2$, and $R^3$ are independently selected from the group consisting of hydrogen, $C_1$-$C_6$ alkyl, $C_3$-$C_8$ cycloalkyl, hydroxy $C_1$-$C_6$ alkyl, halo $C_1$-$C_6$ alkyl, and $C_1$-$C_6$ alkyl carbonyl;

$X^1$ and $X^2$ are independently selected from the group consisting of hydrogen, halo, $C_1$-$C_6$ alkyl, $C_1$-$C_6$ alkoxy, $C_3$-$C_8$ cycloalkyl, hydroxy $C_1$-$C_6$ alkyl, halo $C_1$-$C_6$ alkyl, $C_1$-$C_6$ alkyl carbonyl, $C_2$-$C_6$ alkenyl, $C_2$-$C_6$ alkynyl, $C_6$-$C_{11}$ aryl, $C_3$-$C_7$ heteroaryl, $C_6$-$C_{12}$ aryloxy, CNS, $C_1$-$C_6$ alkoxy carbonyl, $C_1$-$C_6$ alkylthio, mercapto (SH), amido, formyl, and nitro; and $X^3$ and $X^4$ are independently any of $X^1$ and $X^2$, cyano, or isonitrile; and double bond "a" can be cis or trans and double bond "b" can be Z or E;

with the proviso that the compound is not botryllamide C, whereupon the drug resistance is reduced.

By "reducing resistance of a chemotherapeutic agent" is meant that cancer cells that are treated by the chemotherapeutic agent have resistance reversed, development of resistance is reduced, or a combination thereof. For example, the resistance is reduced by at least 5%, at least 10%, at least 20%, at least 30%, at least 40%, at least 50%, at least 60%, at least 70%, or at least 80%.

The chemotherapeutic agent described herein can be any cytotoxic drug that is useful to kill cancer cells. In embodiments, the agent is any drug in which there is resistance to a cancer cell upon administration. For example, the agent can be an antimetabolite (e.g., methotrexate), a mitotic inhibitor (e.g., docetaxel, paclitaxel, vinblastine), an alkylating agent (e.g., cisplatin), a cytotoxic antibiotic (e.g., daunorubicin, doxorubicin, mitoxantrone), a topoisomerase inhibitor (e.g., topotecan, irinotecan), a tyrosine kinase inhibitor (e.g., gefitinib), or any combination thereof. Specific examples of the ABCG2 substrate drug include mitoxantrone, topotecan, irinotecan, SN-38, CPT-11, epirubin, flavopiridol, gefitinib, methotrexate, rhodamine, daunomycin, imatinib, axinitib, bosutinib, cediranib, dasatinib, dasatinib, erlotinib, lapatinib, lestaurtinib, nilotinib, semaxanib, vandetanib, vatalanib, doxorubicin, colchincine, vinblastine, paclitaxel, cisplatin, carboplatin, nedaplatin, oxaliplatin, triplatin tetranitrate, satraplatin, adriamycin, danofloxacin mesylate, docetaxel, and any combination thereof.

Any method known in the art can be used to measure the enhancement of the efficacy of the chemotherapeutic agent and/or the reduction of resistance. The Examples section describes exemplary methods. Alternatively, cells can be contacted with a toxic chemotherapy drug, such as mitoxantrone or topotecan, in an amount that permits cell survival due to the resistance conferred by ABCG2. Cell viability can be measured by a colorimetric assay (Skehan et al., *J. Natl. Cancer Inst.* 82: 1107 1112 (1990)), by counting cells with a cell counter, or by incorporation of tritiated thymidine.

The cells are then contacted with a compound of the invention that inhibits ABCG2. The enhancement of the chemotherapeutic agent and/or reduction of resistance can then be detected by measuring the growth inhibition of cells, using a variety of means, such as $IC_{50}$ measurements, vital staining, metabolite measurements, or confocal microscopy. Confocal microscopy can be used to determine whether a particular drug has been retained or accumulated in the cell.

The invention further provides a method of inhibiting ABCG2 in a mammal afflicted with cancer, which method comprises administering to the mammal an effective amount of a compound selected from the group consisting of

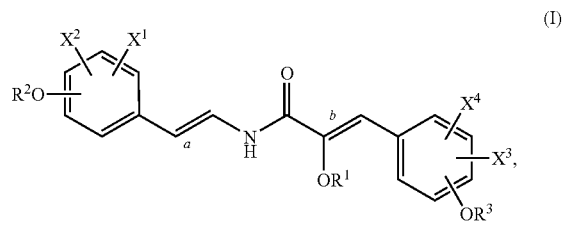
(I)

wherein $R^1$, $R^2$, and $R^3$ are independently selected from the group consisting of hydrogen, $C_1$-$C_6$ alkyl, $C_3$-$C_8$ cycloalkyl, hydroxy $C_1$-$C_6$ alkyl, halo $C_1$-$C_6$ alkyl, and $C_1$-$C_6$ alkyl carbonyl;

$X^1$ and $X^2$ are independently selected from the group consisting of hydrogen, halo, $C_1$-$C_6$ alkyl, $C_1$-$C_6$ alkoxy, $C_3$-$C_8$ cycloalkyl, hydroxy $C_1$-$C_6$ alkyl, halo $C_1$-$C_6$ alkyl, $C_1$-$C_6$ alkyl carbonyl, $C_2$-$C_6$ alkenyl, $C_2$-$C_6$ alkynyl, $C_6$-$C_{11}$ aryl, $C_3$-$C_7$ heteroaryl, $C_6$-$C_{12}$ aryloxy, CNS, $C_1$-$C_6$ alkoxy carbonyl, $C_1$-$C_6$ alkylthio, mercapto (SH), amido, formyl, and nitro; and $X^3$ and $X^4$ are independently any of $X^1$ and $X^2$, cyano, or isonitrile; and double bond "a" can be cis or trans and double bond "b" can be Z or E;

with the proviso that the compound is not botryllamide C, whereupon ABCG2 is inhibited in the mammal.

Since ABCG2 has also been reported to be expressed at high levels in the digestive tract and at the blood-brain barrier (Takano et al., *Pharmacol. Ther.*, 109: 137-61 (2006)), it is envisioned that ABCG2 inhibitors can enhance bioavailability (e.g., oral bioavailability) and brain penetration of ABCG2 substrate drugs, such as, e.g., topotecan. Thus, in an embodiment, the present invention provides a method of increasing the bioavailability of an ABCG2 substrate drug in a mammal, which method comprises administering to the mammal an effective amount of the ABCG2 substrate drug in conjunction with an effective amount of a compound to inhibit ABCG2 protein, said compound being selected from the group consisting of compound of formula (I) to inhibit ABCG2 protein:

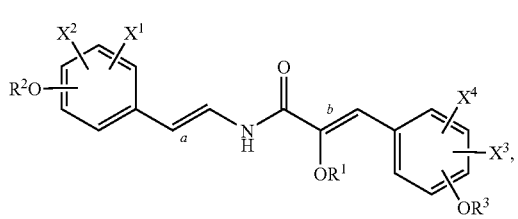

(I)

wherein $R^1$, $R^2$, and $R^3$ are independently selected from the group consisting of hydrogen, $C_1$-$C_6$ alkyl, $C_3$-$C_8$ cycloalkyl, hydroxy $C_1$-$C_6$ alkyl, halo $C_1$-$C_6$ alkyl, and $C_1$-$C_6$ alkyl carbonyl;

$X^1$ and $X^2$ are independently selected from the group consisting of hydrogen, halo, $C_1$-$C_6$ alkyl, $C_1$-$C_6$ alkoxy, $C_3$-$C_8$ cycloalkyl, hydroxy $C_1$-$C_6$ alkyl, halo $C_1$-$C_6$ alkyl, $C_1$-$C_6$ alkyl carbonyl, $C_2$-$C_6$ alkenyl, $C_2$-$C_6$ alkynyl, $C_6$-$C_{11}$ aryl, $C_3$-$C_7$ heteroaryl, $C_6$-$C_{12}$ aryloxy, CNS, $C_1$-$C_6$ alkoxy carbonyl, $C_1$-$C_6$ alkylthio, mercapto (SH), amido, formyl, and nitro; and $X^3$ and $X^4$ are independently any of $X^1$ and $X^2$, cyano, or isonitrile; and double bond "a" can be cis or trans and double bond "b" can be Z or E;

with the proviso that the compound is not botryllamide C, whereupon the bioavailability of the ABCG2 substrate drug is improved.

Since CNS penetration can be enhanced by administration of a compound of the invention, such method is useful in the treatment of cancer, such as brain tumors, CNS metastases, and/or gastrointestinal stromal tumors.

The ABCG2 substrate drug can be, for example, an antimetabolite (e.g., methotrexate), a mitotic inhibitor (e.g., docetaxel, paclitaxel, vinblastine), an alkylating agent (e.g., cisplatin), a cytotoxic antibiotic (e.g., daunorubicin, doxorubicin, mitoxantrone), a topoisomerase inhibitor (e.g., topotecan, irinotecan), a tyrosine kinase inhibitor (e.g., gefitinib), or any combination thereof. Specific examples of the ABCG2 substrate drug include mitoxantrone, topotecan, irinotecan, SN-38, CPT-11, epirubin, flavopiridol, gefitinib, methotrexate, rhodamine, daunomycin, imatinib, axinitib, bosutinib, cediranib, dasatinib, dasatinib, erlotinib, lapatinib, lestaurtinib, nilotinib, semaxanib, vandetanib, vatalanib, doxorubicin, colchincine, vinblastine, paclitaxel, cisplatin, carboplatin, nedaplatin, oxaliplatin, iriplatin tetranitrate, satraplatin, adriamycin, danofloxacin mesylate, docetaxel, and any combination thereof. In some embodiments, the ABCG2 substrate drug is mitoxantrone, topotecan, irinotecan, flavopiridol, gefitinib, and/or methotrexate.

Pgp, MRP1, and ABCG2 are major contributors to multi-drug resistance in most cancer cells in culture (Szakacs et al., *Nat. Rev. Drug Discov.*, 5: 219-34 (2006)). ABCG2 has overlapping substrate specificity with MRP1 and Pgp. Accordingly, in an embodiment, the present invention provides a method of inhibiting MRP1 in a mammal afflicted with cancer, which method comprises administering to the mammal an effective amount of a compound of formula (I) to inhibit ABCG2 protein:

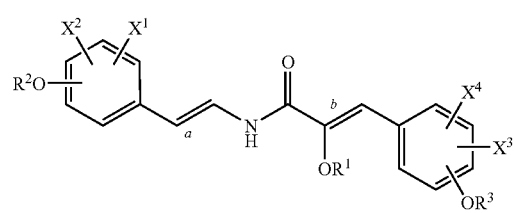

(I)

wherein $R^1$, $R^2$, and $R^3$ are independently selected from the group consisting of hydrogen, $C_1$-$C_6$ alkyl, $C_3$-$C_8$ cycloalkyl, hydroxy $C_1$-$C_6$ alkyl, halo $C_1$-$C_6$ alkyl, and $C_1$-$C_6$ alkyl carbonyl;

$X^1$ and $X^2$ are independently selected from the group consisting of hydrogen, halo, $C_1$-$C_6$ alkyl, $C_1$-$C_6$ alkoxy, $C_3$-$C_8$ cycloalkyl, hydroxy $C_1$-$C_6$ alkyl, halo $C_1$-$C_6$ alkyl, $C_1$-$C_6$ alkyl carbonyl, $C_2$-$C_6$ alkenyl, $C_2$-$C_6$ alkynyl, $C_6$-$C_{11}$ aryl, $C_3$-$C_7$ heteroaryl, $C_6$-$C_{12}$ aryloxy, CNS, $C_1$-$C_6$ alkoxy carbonyl, $C_1$-$C_6$ alkylthio, mercapto (SH), amido, formyl, and nitro; and $X^3$ and $X^4$ are independently any of $X^1$ and $X^2$, cyano, or isonitrile; and double bond "a" can be cis or trans and double bond "b" can be Z or E;

with the proviso that the compound is not botryllamide C, whereupon MRP1 is inhibited in the mammal.

All of the methods described herein have applicability to the treatment of any type of cancer that over-expresses ABCG2 (and/or MRP1) and is capable of being treated with a chemotherapeutic agent. Such cancers include, for example, leukemias (e.g., acute myeloid leukemia (AML), chronic myeloid leukemia (CML)), solid tumors (e.g., of the lung, endometrium, or digestive tract), melanomas, non-small cell lung cancer tumors, colon tumors, prostate tumors, brain tumors, lymphomas, breast tumors, ovarian tumors, lung tumors, and stomach tumors.

For purposes of the present inventive methods, the mammal includes, without limitation, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In accordance with any of the embodiments of the invention, $R^1$ is hydrogen or $C_1$-$C_6$ alkyl, preferably methyl. In accordance with any of the embodiments of the invention, $R^2$ is hydrogen or $C_1$-$C_6$ alkyl, preferably methyl.

In accordance with any of the embodiments of the invention, $X^1$ and $X^2$ are independently selected from the group consisting of hydrogen and halo. Any suitable halo (fluoro, chloro, bromo, or iodo) can be employed, preferably bromo. For example, in embodiments of the invention, one of $X^1$ and $X^2$ is hydrogen and the other of $X^1$ and $X^2$ is bromo.

In accordance with any of the embodiments of the invention, $R^3$ is hydrogen or cyano. In accordance with any of the embodiments of the invention, $R^2$ and $R^3$, other than hydrogen, are in the ortho, meta, or preferably para position of the phenyl rings to which they are attached.

In accordance with any of the embodiments of the invention, the compound is selected from the group consisting of botryllamide A, botryllamide B, botryllamide D, botryllamide E, botryllamide F, botryllamide G, botryllamide I, botryllamide J, and any combination thereof, particularly botryllamide I or botryllamide J.

The present invention also provides an isolated or purified compound selected from the group consisting of botryllamide I and botryllamide J.

The present invention further provides a pharmaceutical composition comprising a pharmaceutically acceptable carrier and a compound selected from the group consisting of botryllamide I and botryllamide J.

The present invention further provides a pharmaceutical composition comprising a pharmaceutically acceptable carrier and any of the compounds described above.

The invention further provides a compound of formula (II):

(II)

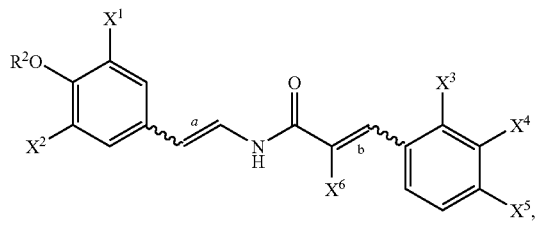

wherein $R^2$ is selected from the group consisting of hydrogen, $C_1$-$C_6$ alkyl, $C_3$-$C_8$ cycloalkyl, hydroxy $C_1$-$C_6$ alkyl, halo $C_1$-$C_6$ alkyl, and $C_1$-$C_6$ alkyl carbonyl;

$X^1$, $X^2$, and $X^6$ are independently selected from the group consisting of hydrogen, halo, $C_1$-$C_6$ alkyl, $C_1$-$C_6$ alkoxy, $C_3$-$C_8$ cycloalkyl, hydroxy $C_1$-$C_6$ alkyl, halo $C_1$-$C_6$ alkyl, $C_1$-$C_6$ alkyl carbonyl, $C_2$-$C_6$ alkenyl, $C_2$-$C_6$ alkynyl, $C_6$-$C_{11}$ aryl, $C_3$-$C_7$ heteroaryl, $C_6$-$C_{12}$ aryloxy, CNS, $C_1$-$C_6$ alkoxy carbonyl, $C_1$-$C_6$ alkylthio, mercapto (SH), amido, formyl, and nitro; and $X^3$ and $X^4$ are independently any of $X^1$ and $X^2$, cyano, or isonitrile;

$X^5$ is selected from the group consisting of hydrogen, hydroxy, halo, $C_1$-$C_6$ alkyl, $C_1$-$C_6$ alkoxy, $C_3$-$C_8$ cycloalkyl, hydroxy $C_1$-$C_6$ alkyl, halo $C_1$-$C_6$ alkyl, $C_1$-$C_6$ alkyl carbonyl, $C_2$-$C_6$ alkenyl, $C_2$-$C_6$ alkynyl, $C_6$-$C_{11}$ aryl, $C_3$-$C_7$ heteroaryl, $C_6$-$C_{12}$ aryloxy, CNS, $C_1$-$C_6$ alkoxy carbonyl, $C_1$-$C_6$ alkylthio, mercapto (SH), amido, formyl, and nitro; and double bond "a" can be cis or trans and double bond "b" can be Z or E; with the provisos that (1) when $X^5$ is hydrogen or hydroxy, $X^3$ and $X^4$ are hydrogen, $X^1$ and $X^2$ are hydrogen or halo, $R^2$ is hydrogen or methyl, $X^6$ is not alkoxy, e.g., not methoxy; and (2) when $R^2$, $X^1$, $X^2$, and $X^5$ are hydrogen, $X^4$ and $X^6$ are hydroxy, then $X^3$ is not NC.

In accordance with the invention, the alkyl group or alkyl portion of a group containing an alkyl segment can be linear or branched, e.g., methyl, ethyl, propyl, n-butyl, sec-butyl, t-butyl, n-pentyl, iso-pentyl, and the like. Alkenyl can be linear or branched. Aryl can be phenyl or naphthyl. Heteroaryl can be an aromatic group having a heteroatom such as O, N, or S.

In accordance with an embodiment of the invention, in the compound of formula (II), $X^1$, $X^2$, and $X^6$ are independently selected from the group consisting of hydrogen, halo, $C_1$-$C_6$ alkyl, or $C_1$-$C_6$ alkoxy, particularly hydrogen. In any of the embodiments of formula (II), $X^1$, $X^2$, and $X^6$ are halo. In any of the embodiments of formula (II), $X^1$, $X^2$, and $X^6$ are $C_1$-$C_6$ alkyl. In any of the embodiments of formula (II), $X^1$, $X^2$, and $X^6$ are $C_1$-$C_6$ alkoxy.

In any of the embodiments of formula (II), $X^3$ and $X^4$ are independently any of $X^1$ and $X^2$, cyano, or isonitrile.

In any of the embodiments of formula (II), $X^3$ and $X^4$ are independently any of $X^1$ and $X^2$.

In any of the embodiments of formula (II), $X^5$ is selected from the group consisting of hydrogen, hydroxy, halo, $C_1$-$C_6$ alkyl, $C_1$-$C_6$ alkoxy, $C_3$-$C_8$ cycloalkyl, hydroxy $C_1$-$C_6$ alkyl, halo $C_1$-$C_6$ alkyl, $C_1$-$C_6$ alkyl carbonyl, $C_2$-$C_6$ alkenyl, $C_2$-$C_6$ alkynyl, $C_6$-$C_{11}$ aryl, $C_3$-$C_7$ heteroaryl, $C_6$-$C_{12}$ aryloxy, CNS, $C_1$-$C_6$ alkoxy carbonyl, $C_1$-$C_6$ alkylthio, mercapto (SH), amido, formyl, and nitro, particularly, $X^5$ is selected from the group consisting of hydrogen, hydroxy, halo, $C_1$-$C_6$ alkyl, and $C_1$-$C_6$ alkoxy. In embodiments of formula (II), $X^5$ is hydrogen. In embodiments of formula (II), $X^5$ is hydroxy. In certain embodiments of formula (II), $X^5$ is $C_1$-$C_6$ alkyl. In certain other embodiments of formula (II), $X^5$ is $C_1$-$C_6$ alkoxy.

The compounds of formula (II), which overlap with those of formula (I), are intended for the same uses and methods as described above for the compounds of formula (I).

Accordingly, the invention provides a pharmaceutical composition comprising a pharmaceutically acceptable carrier and a compound of formula (II). The invention also provides a method of enhancing the chemotherapeutic treatment of tumor cells in a mammal with a chemotherapeutic agent, which method comprises administering to the mammal an effective amount of the chemotherapeutic agent in conjunction with an effective amount of a compound of formula (II) to inhibit the ABCG2 protein, a method of inhibiting ABCG2 in a mammal afflicted with cancer, which method comprises administering to the mammal an effective amount of a compound of formula (II), a method of reducing drug resistance to chemotherapeutic agents by inhibiting ABCG2 in a mammal, which method comprises administering to the mammal an effective amount of a compound of formula (II), a method of increasing the bioavailability of an ABCG2 substrate drug in a mammal, which method comprises administering to the mammal an effective amount of the ABCG2 substrate drug in conjunction with an effective amount of a compound to inhibit ABCG2 protein, wherein said compound is a compound of formula (II), a method of inhibiting MRP1 in a mammal afflicted with cancer, which method comprises administering to the mammal an effective amount of a compound of formula (II), or a method of inhibiting Pgp in a mammal afflicted with cancer, which method comprises administering to the mammal an effective amount of a compound of formula (II).

The invention also provides the use of a compound of formula (II) in the preparation of a medicament for (i) enhancing the chemotherapeutic treatment of tumor cells in a mammal in combination with a chemotherapeutic agent, (ii) inhibiting ABCG2 protein in a cancer patient, (iii) reducing drug resistance of a chemotherapeutic agent in a cancer patient, (iv) increasing the bioavailability of an ABCG2 substrate drug in a cancer patient, (v) inhibiting MRP1 in a cancer patient, or (vi) inhibiting Pgp in a cancer patient.

The present invention further provides a method of enhancing the chemotherapeutic treatment of tumor cells in a mammal with a chemotherapeutic agent, which method comprises administering to the mammal an effective amount of the chemotherapeutic agent in conjunction with an effective amount of a compound to inhibit ABCG2 protein, wherein said compound is selected from the group consisting of

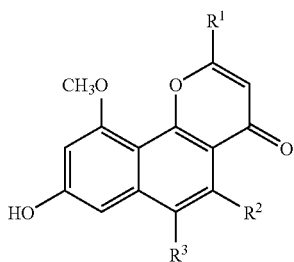

5: $R^1 = CH_3, R^2 = OH, R^3 = H$,
6: $R^1 = CH_3, R^2 = OH, R^3 = OCH_3$
7: $R^1 = CH_3, R^2 = OCH_3, R^3 = OCH_3$
8: $R^1 = CH_2CH_2CH_3, R^2 = OH, R^3 = H$
9: $R^1 = CH_2CH_2CH_3, R^2 = OH, R^3 = OCH_3$
10: $R^1 = CH_2CH_2CH_3, R^2 = OCH_3, R^3 = H$
11: $R^1 = CH_2CH_2CH_3, R^2 = OCH_3, R^3 = OCH_3$, and any combination thereof, whereupon the chemotherapeutic treatment is enhanced.

The present invention further provides a method of inhibiting ABCG2 in a mammal, which method comprises administering to the mammal an effective amount of a compound selected from the group consisting of

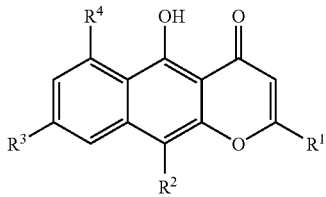

1: $R^1 = CH_3, R^2 = H, R^3 = OH, R^4 = OCH_3$
2: $R^1 = CH_3, R^2 = OCH_3, R^3 = OCH_3, R^4 = OH$
3: $R^1 = CH_2CH_2CH_3, R^2 = H, R^3 = OH, R^4 = OCH_3$
4: $R^1 = CH_2CH_2CH_3, R^2 = OCH_3, R^3 = OCH_3, R^4 = OH$,

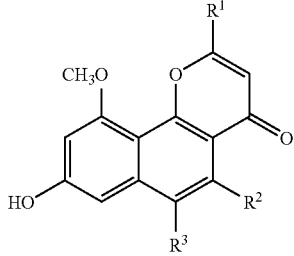

5: $R^1 = CH_3, R^2 = OH, R^3 = H$,
6: $R^1 = CH_3, R^2 = OH, R^3 = OCH_3$
7: $R^1 = CH_3, R^2 = OCH_3, R^3 = OCH_3$
8: $R^1 = CH_2CH_2CH_3, R^2 = OH, R^3 = H$
9: $R^1 = CH_2CH_2CH_3, R^2 = OH, R^3 = OCH_3$
10: $R^1 = CH_2CH_2CH_3, R^2 = OCH_3, R^3 = H$
11: $R^1 = CH_2CH_2CH_3, R^2 = OCH_3, R^3 = OCH_3$, and any combination thereof, whereupon ABCG2 is inhibited in the mammal.

The present invention also provides a method of reducing drug resistance of cancer to chemotherapeutic agents by inhibiting ABCG2 in a mammal, which method comprises administering to the mammal an effective amount of a compound selected from the group consisting of

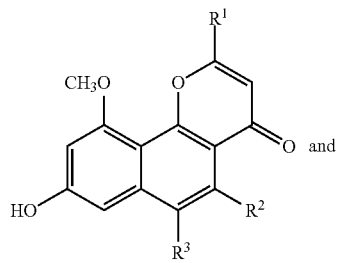

5: $R^1 = CH_3, R^2 = OH, R^3 = H$,
6: $R^1 = CH_3, R^2 = OH, R^3 = OCH_3$
7: $R^1 = CH_3, R^2 = OCH_3, R^3 = OCH_3$
8: $R^1 = CH_2CH_2CH_3, R^2 = OH, R^3 = H$
9: $R^1 = CH_2CH_2CH_3, R^2 = OH, R^3 = OCH_3$
10: $R^1 = CH_2CH_2CH_3, R^2 = OCH_3, R^3 = H$ and
11: $R^1 = CH_2CH_2CH_3, R^2 = OCH_3, R^3 = OCH_3$, and any combination thereof, whereupon drug resistance of cancer is reduced in the mammal.

The present invention further provides a method of increasing the bioavailability of an ABCG2 substrate drug in a mammal, which method comprises administering to the mammal an effective amount of the ABCG2 substrate drug in conjunction with an effective amount of a compound to inhibit ABCG2, wherein said compound is selected from the group consisting of:

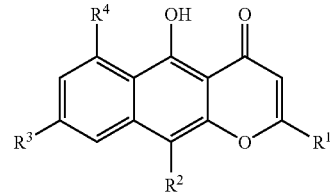

1: $R^1 = CH_3, R^2 = H, R^3 = OH, R^4 = OCH_3$
2: $R^1 = CH_3, R^2 = OCH_3, R^3 = OCH_3, R^4 = OH$
3: $R^1 = CH_2CH_2CH_3, R^2 = H, R^3 = OH, R^4 = OCH_3$
4: $R^1 = CH_2CH_2CH_3, R^2 = OCH_3, R^3 = OCH_3, R^4 = OH$,

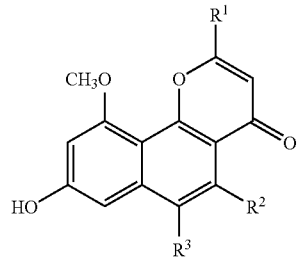

5: $R^1 = CH_3, R^2 = OH, R^3 = H$,
6: $R^1 = CH_3, R^2 = OH, R^3 = OCH_3$
7: $R^1 = CH_3, R^2 = OCH_3, R^3 = OCH_3$
8: $R^1 = CH_2CH_2CH_3, R^2 = OH, R^3 = H$
9: $R^1 = CH_2CH_2CH_3, R^2 = OH, R^3 = OCH_3$
10: $R^1 = CH_2CH_2CH_3, R^2 = OCH_3, R^3 = H$
11: $R^1 = CH_2CH_2CH_3, R^2 = OCH_3, R^3 = OCH_3$, and any combination thereof, whereupon the bioavailability is increased.

Generally, the compounds of the invention will be administered in a pharmaceutical composition to an individual afflicted with a cancer. Those undergoing or about to undergo chemotherapy can be treated with at least one compound described herein separately or in conjunction with other treatments, as appropriate. In therapeutic applications, compositions are administered to a patient in an amount sufficient to elicit an effective depression of ABCG2 activity thereby potentiating the cytotoxicity of the chemotherapeutic treatment. A dose adequate to accomplish this is defined as an "effective amount," which is also an "ABCG2 inhibiting effective amount." Amounts effective for a therapeutic or prophylactic use will depend on, e.g., the stage and severity of the disease being treated, the age, weight, and general state of health of the patient, and the judgment of the prescribing physician. The size of the dose will also be determined by the compound selected, method of administration, timing and frequency of administration as well as the existence, nature, and extent of any adverse side-effects that might accompany the administration of a particular compound and the desired physiological effect. It will be appreciated by one of skill in the art that various disease states may require prolonged treatment involving multiple administrations, perhaps using a series of different ABCG2 inhibitors and/or chemotherapeutic agents in each or various rounds of administration.

Suitable chemotherapeutic agents administered in coordination with at least one compound of the present invention include mitoxantrone, topotecan, irinotecan, flavopiridol, gefitinib, methotrexate, rhodamine, daunomycin, imatinib, doxorubicin, colchincine, vinblastine, paclitaxel, cisplatin, adriamycin, danofloxacin mesylate, and/or docetaxel. The chemotherapeutic agent is administered in a dose sufficient to treat the cancer (e.g., cancer-treatment effective amount of a chemotherapeutic agent). Such doses are known in the art (see, for example, the *Physicians' Desk Reference* (2004)). Such agents can be administered using techniques such as those described in, for example, Wasserman et al., *Cancer*, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present inventive methods can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response, e.g., as determined by measuring cancer-specific antigens or other measurable parameters related to the tumor load of a patient.

Any of the compounds of the invention can be administered in a dose sufficient to enhance the effect of the chemotherapeutic agent and/or reduce drug resistance in a cancer. A suitable dosage is that which will result in a concentration of the compound of the invention in the cancerous cells to be treated sufficient to inhibit ABCG2 activity, e.g., from about 10 nM to 200 nM intracellularly, which can require an extracellular concentration of from about 10 µM to 50 µM. The dose can be adjusted as necessary to enhance the effect of the chemotherapeutic agent and/or reduce drug resistance.

The pharmaceutical compositions for therapeutic treatment are intended for any suitable mode of administration, including parenteral, topical, oral, or local administration and generally comprise a pharmaceutically acceptable carrier and an amount of the active ingredient sufficient to reduce, and preferably prevent, the activity of ABCG2. The carrier can be any of those conventionally used and is limited only by chemico-physical considerations, such as solubility and lack of reactivity with the compound of the invention, and by the route of administration.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Preferably a compound of the invention and a chemotherapeutic agent are coadministered to the mammal. By "coadministering" is meant administering the chemotherapeutic agent and a compound of the invention sufficiently close in time such that a compound of the invention can enhance the effect of the chemotherapeutic agent. In this regard, a compound of the invention can be administered first and the chemotherapeutic agent can be administered second, or vice versa. Alternatively, a compound of the invention and the chemotherapeutic agent can be administered simultaneously. In addition, a combination of compounds of the invention can be administered, and one or more of the compounds of the invention can be administered in combination with another agent useful in the treatment of cancer.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as polyethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-1'-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophils balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound of the present invention, alone or in combination with other suitable components, can be made into aerosol formulations to be administered via inhalation. A compound of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, a compound of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The concentration of a compound of the present invention in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Thus, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, a compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The following examples further illustrate the invention but, of course, should not be construed as in any way limiting its scope.

EXAMPLE 1

This example illustrates a method of isolating botryllamides in accordance with an embodiment of the invention. The marine ascidian *Botryllus tyreus* (75.5 g wet weight) is sequentially extracted with 1:1 $CH_2Cl_2$-MeOH and 100% MeOH. Evaporation of the solvents under reduced pressure provides 4.8 g of crude extract. A 3 g aliquot of the extract is dissolved in 90% aq. MeOH and then extracted with n-hexane. The aqueous MeOH fraction is further diluted with $H_2O$ to provide a 60% aq. MeOH solution, which is then partitioned with $CH_2Cl_2$. The bioactive $CH_2Cl_2$ fraction is separated by ODS ($C_{18}$) flash chromatography eluted with a step gradient of 1:1 MeOH—$H_2O$, 4:1 MeOH—$H_2O$ and 100% MeOH. Final purification by ODS HPLC elutes with a linear gradient from 20% $CH_3CN$-80% $H_2O$ to 70% $CH_3CN$-30% $H_2O$ over 50 minutes afforded botryllamide A (110 mg), botryllamide B (3.5 mg), botryllamide C (29 mg), botryllamide D (2.5 mg), botryllamide E (58 mg), botryllamide F (1.2 mg), botryllamide G (9 mg), botryllamide H (4.0 mg), botryllamide I (4.7 mg) and botryllamide J (1.6 mg).

EXAMPLE 2

This example demonstrates a screening assay for ABCG2 inhibitors in accordance with an embodiment of the invention.

Accumulation of pheophorbide a, a fluorescent ABCG2 substrate (Jonker et al., *Proc. Natl. Acad. Sci. USA*, 99: 15649-54 (2002) and Robey et al., *Cancer Res.*, 64: 1242-6 (2004)), formed the basis of the assay for inhibitors of ABCG2 activity (Henrich et al., *J. Biomol. Screen*, 11: 176-83 (2006)). Briefly, NCI-H460/MX20 cells are transferred to black wall, clear bottom 384-well polylysine-coated assay plates (Corning, Corning, N.Y.) and allowed to attach for several hours. Pheophorbide a (1 µM final concentration) is added immediately followed by compounds or vehicle (DMSO/PBS) control and incubated an additional 18 h. After removal of medium and washing with PBS containing $Ca^{2+}$ and $Mg^{2+}$, fluorescence intensity is read on a Tecan Safire fluorescence plate reader in bottom read mode, 395 nm excitation, and 670 nm emission. Each plate has control wells containing 10 µM (final concentration) FTC. Data are normalized to FTC and reported as % of FTC fluorescence.

Table 1 summarizes the activities of compounds in accordance with an embodiment of the invention in the pheophorbide a accumulation assay, as well as other activities discussed in Example 3.

EXAMPLE 3

This example demonstrates an assay to determine the ability of compounds to sensitize cancer cells to killing by mitoxantrone in accordance with an embodiment of the invention.

The ability of compounds to sensitize NCI-H460/MX20 cells to killing by mitoxantrone is assessed as described in Henrich et al. (*J. Biomol. Screen*, 11: 176-83 (2006)). ABCG2 over-expressing cells or parental cells are treated with mitoxantrone in the presence or absence of 10 µM compound (or 1 µM FTC) and cell numbers assessed after 2 d by an XTT assay (Scudiero et al., *Cancer Res.*, 48: 4827-33 (1988)). Final DMSO concentration is 0.2% (v/v). Compounds in accordance with an embodiment of the invention can inhibit ABCG2-mediated transport using BODIPY-prazosin as a substrate. For details of the test, see Robey et al., *Br. J. Cancer*, 89: 1971-8 (2003). This example also demonstrates that exemplary compounds inhibit MRP1-mediated calcein efflux (Robey et al., 2003, vide supra and Alvarez et al., *Mol. Pharmacol.*, 54: 802-14 (1998)). Transfected HEK293 cells expressing ABCG2, Pgp, or MRP1 are trypsinized and incubated in complete medium (phenol red-free Richter's medium with 10% FCS and penicillin/streptomycin) containing 200 nM BODIPY-prazosin, 0.5 µg/ml rhodamine 123 or 200 nM calcein AM, respectively, in the presence or absence of the desired concentration of inhibitor for 30 min at 37° C. The positive controls for inhibition of ABC transporters are 10 µM FTC for ABCG2, 3 µg/ml valspodar for Pgp and 25 µM MK-571 for MRP1. Cells are then washed and incubated in substrate-free medium continuing with or without inhibitor for 1 h.

TABLE 1

Effects of botryllamide compounds in multiple assays

| Compound | Pheophorbide a [a]max activity, % (80 µM) | IC50 (µM) | MX sensitization (@ 10 µM)[b] | ABCG2 Flow-BODIPY-prazosin[c] | ABCG2 Flow-MX | Flow-Pgp, Fold Increase[d] | Flow-MRP1, Fold Increase[e] |
|---|---|---|---|---|---|---|---|
| Botryllamide A | 89.7 | 33 | + | + | + | 17.63 | 4.5 |
| Botryllamide B | 84.3 (40 µM) | 11.2 | + | + | + | 1.95 | 3.26 |
| Botryllamide D | 63.5 | 16.4 | + | + | + | 1.49 | 2.39 |
| Botryllamide E | 68.8 | 23.3 | + | + | + | 0.76 | 1.96 |
| Botryllamide F | 81.0 | 16.7 | + | + | + | 0.59 | 3.33 |
| Botryllamide G | 123.7 (40 µM) | 6.9 | + | + | + | 0.68 | 2.1 |
| Botryllamide I | 71.3 | 41.4 | + | + | + | 0.8 | 3.14 |
| Botryllamide J | 70.5 | 26.9 | − | + | + | 0.58 | 2.54 |

[a] % of FTC response
[b] % NCI-H460/MX20 cell survival in the presence of compound and mitoxantrone
[c] BODIPY-prazosin efflux: treated/control ratio at 10 µM compound
[d] Pgp inhibition, rhodamine efflux: treated/control ratio at 10 µM compound
[e] MRP1 inhibition, calcein efflux: treated/control ratio at 10 µM compound

EXAMPLE 4

This example illustrates a method of isolation of naphthopyrones in accordance with an embodiment of the invention. The compounds are isolated from two marine echinoderms, the sea star *Capillaster multiradiatus* and a taxonomically undefined crinoid. The marine samples are sequentially extracted with 1:1 $CH_2Cl_2$-MeOH and 100% MeOH to provide organic solvent extracts. A 1 g aliquot of the extract from *Capillaster multiradiatus* is subjected to a solvent-solvent partitioning scheme that concentrated the ABCG2 inhibitory activity into the EtOAc soluble fraction. This fraction is chromatographed on Sephadex LH-20 with 1:1 $CH_2Cl_2$-MeOH. Final purification by $C_{18}$ reversed-phase HPLC, eluting with a linear gradient from 75:25 MeOH/$H_2O$ to 100% MeOH, provide compounds 1 (1.0 mg), 3 (2.1 mg), 5 (2.4 mg) and 8 (3.1 mg).

A 2.0 g aliquot of the extract from the as yet undefined crinoid is also subjected to a solvent-solvent partitioning scheme that concentrated the activity into the EtOAc and MeOtBu soluble fractions. The EtOAc fraction is chromatographed on Sephadex LH-20 with 2:5:1 hexane-$CH_2Cl_2$-MeOH and the active fractions were subjected to $C_{18}$ reversed-phase HPLC as above to yield compounds 2 (1.8 mg), 4 (3.2 mg), 7 (5.6 mg), 9 (5.3 mg) and 10 (2.1 mg). The MeOtBu fraction is chromatographed on Sephadex LH-20 with 1:1 $CH_2Cl_2$-MeOH and further purified by HPLC as described above to yield compounds 6 (1.0 mg) and 11 (1.1 mg).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified compound selected from the group consisting of botryllamide I and botryllamide J.

2. A pharmaceutical composition comprising a pharmaceutically acceptable carrier and a compound selected from the group consisting of botryllamide I and botryllamide J.

3. A method of inhibiting Pgp in a mammal afflicted with cancer, which method comprises administering to the mammal a pharmaceutical composition according to claim 2.

* * * * *